(12) United States Patent
Markham et al.

(10) Patent No.: US 6,965,005 B2
(45) Date of Patent: Nov. 15, 2005

(54) MOLD INHIBITOR INTEGRATED WITHIN A MATRIX AND METHOD OF MAKING SAME

(76) Inventors: Joseph P. Markham, 12094 W. 75th Pl., Arvada, CO (US) 80005; Thomas Kieth Martin, 104 Crestway Ter., Amarillo, TX (US) 79106

( * ) Notice: Subject to any disclaimer, the term of this patent is extended or adjusted under 35 U.S.C. 154(b) by 0 days.

(21) Appl. No.: 10/962,634

(22) Filed: Oct. 11, 2004

(65) Prior Publication Data

US 2005/0065308 A1 Mar. 24, 2005

Related U.S. Application Data

(62) Division of application No. 10/839,541, filed on May 4, 2004, which is a continuation of application No. 10/431,488, filed on May 6, 2003.

(51) Int. Cl.$^7$ .............................................. C08L 89/00
(52) U.S. Cl. .............................. 528/3; 524/27; 424/602; 424/484; 424/488
(58) Field of Search ............................ 528/3; 524/27; 424/602, 484, 488

(56) References Cited

U.S. PATENT DOCUMENTS

| | | | |
|---|---|---|---|
| 3,119,691 A | 1/1964 | Ludington et al. ................. 99/2 |
| 3,284,211 A | 11/1966 | Williams ........................... 99/2 |
| 3,467,525 A | 9/1969 | Hale et al. ......................... 99/2 |
| 3,665,998 A | 5/1972 | Nowak .......................... 164/76 |
| 3,725,324 A | 4/1973 | Cummisford |
| 3,754,961 A | 8/1973 | Ueno et al. ..................... 117/16 |
| 3,808,340 A | 4/1974 | Palmer .......................... 426/92 |
| 3,882,255 A | 5/1975 | Gorham, Jr. et al. ......... 426/235 |
| 3,958,009 A * | 5/1976 | Lepore et al. ................ 514/557 |
| 4,000,319 A | 12/1976 | Eichelburg ....................... 426/2 |
| 4,039,687 A | 8/1977 | Weyn ............................ 426/62 |
| 4,104,407 A | 8/1978 | Stringer et al. ................. 426/99 |
| 4,143,169 A | 3/1979 | Skoch et al. .................. 426/307 |
| 4,145,447 A | 3/1979 | Fisher et al. ................... 426/72 |
| 4,162,336 A | 7/1979 | Brown, Jr. et al. .......... 426/623 |
| 4,229,485 A | 10/1980 | Brown et al. ................ 426/305 |
| 4,388,302 A | 6/1983 | Ecanow |
| 4,410,551 A | 10/1983 | Comer ........................... 426/99 |
| 4,454,804 A | 6/1984 | McCulloch ................... 99/348 |
| 4,592,913 A | 6/1986 | Hara ............................ 426/104 |
| 4,617,328 A | 10/1986 | Liu |
| 4,659,583 A | 4/1987 | Hashimoto et al. .......... 426/629 |
| 4,713,250 A | 12/1987 | Tonyes et al. ................... 426/2 |
| 4,735,812 A | 4/1988 | Bryson et al. ............... 426/262 |
| 4,879,850 A | 11/1989 | Glassco et al. |
| 5,071,665 A | 12/1991 | Buckley et al. .............. 426/272 |
| 5,224,315 A | 7/1993 | Winter, IV |
| 5,373,674 A | 12/1994 | Winter, IV |
| 5,497,594 A | 3/1996 | Giuseppe et al. |
| 5,710,190 A | 1/1998 | Jane et al. |
| 5,713,526 A | 2/1998 | Martin et al. .................. 241/74 |
| 5,820,039 A | 10/1998 | Martin et al. ................... 241/7 |
| 5,858,436 A * | 1/1999 | Bompeix et al. ............. 426/321 |
| 5,894,029 A | 4/1999 | Brown et al. ................ 426/302 |
| 6,414,044 B2 | 7/2002 | Taylor |
| 6,433,034 B1 | 8/2002 | Leenslag et al. |

OTHER PUBLICATIONS

Wharton et al.; "Temporal synthesis and radiolabelling of the sorghum 3-deoxyanthocyanidin phytoalexins and the anthocyanin, cyanidin 3-dimalonyl glucoside"; RESEARCH New Phtol. (2000); vol. 145; pp. 457–469.

Nicholson et al; "Phytoalexin synthesis by the sorghum mesocotyl in response to infection by pathogenic and non-pathogenic fungi"; Proc. Natl. Acad. Sci. USA vol. 84, Aug. 1987 Applied Biology; pps. 5520–5524.

Host Defense: Sorghum Anthracnose Diseases; http://www.sorghumanthracnose.org/hostdef.html; 4 pages.

Wharton et al.; "Determination of the Temporal Synthesis of Sorghum Phytoalexins Using Photodiode Array–HPLC and Maldi–Mass Spectrometry"; http://www.bspp.org.uk/icpp98/1.9/13.html; 2 pages.

Product Brochure for Biofoam packaging material: 4 pages, Biofoam Corporation, 918 South Park Lane, Tempe arizona 85281.

Explanation of Reference BK (Product Brochure for Biofoam packaging material).

* cited by examiner

Primary Examiner—James J. Seidleck
Assistant Examiner—Irina S. Zemel
(74) Attorney, Agent, or Firm—Sheridan Ross P.C.

(57) ABSTRACT

The invention provides a composition useful in the construction industry for the prevention or remediation of mold growth in a man made structure. The composition contains an extruded milo matrix incorporating terpenes, phytoalexins, calcium propionate or combinations of these chemicals having antifungal activity. Methods of making and using the compositions are also disclosed.

33 Claims, 1 Drawing Sheet

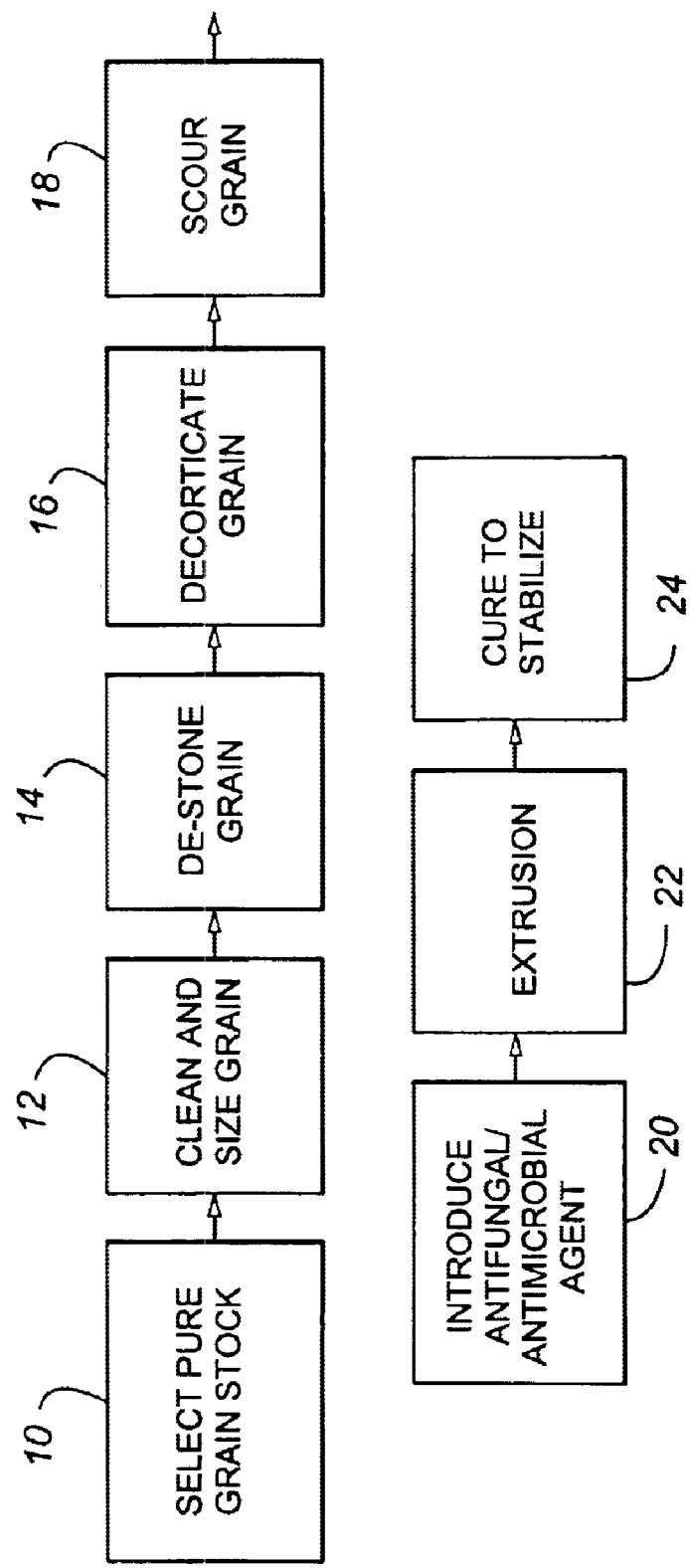

MOLD INHIBITOR INTEGRATED WITHIN A MATRIX AND METHOD OF MAKING SAME

CROSS REFERENCE TO RELATED APPLICATIONS

This application is a divisional application of copending application Ser. No. 10/839,541, filed on May 4, 2004, which is a continuation-in-part application of copending application Ser. No. 10/431,488, filed on May 6, 2003, the disclosures of which are incorporated herein by reference.

FIELD OF THE INVENTION

The present invention relates to the production of anti-microbial and anti-fungal materials, and more particularly to a mold inhibitor integrated within a natural matrix and a method of making the same.

BACKGROUND OF THE INVENTION

In the construction or building industry, it is known to incorporate various anti-microbial and anti-fungal agents within construction materials to enhance the ability of the construction materials to inhibit undesirable growth of microbes or mold. Particularly in humid and wet climates, microbial and mold growth in building materials can cause many health related problems.

One example of a reference disclosing building materials which may incorporate such anti-fungal/microbial agents is U.S. Pat. No. 4,879,850. The construction material disclosed therein includes a strawboard made of cereal stocks such as rice, wheat, rye, oats and barley, the strawboard being manufactured through an extrusion process. Anti-fungal agents, anti-bacterial agents, mold inhibitors, rodenticides and the like may be added as ingredients to the strawboard composition, or may be applied as coatings.

A reference disclosing a foamed material which may be used for insulation and which incorporates an anti-microbial agent is U.S. Pat. No. 5,710,190. The insulation material is a soy protein-based thermoplastic composition. The composition is made of soy protein combined with a foaming agent, an organic plastisizing agent, an aqueous medium such as water, and additives as desired. Articles formed from the composition have a foamed, cellular structure. The thermoplastic compositions are prepared by mixing together the components, and then molding the components by a compression molding process. Alternatively, the composition may be extruded to produce pellets. The anti-microbial agents disclosed, such as fungicides or bactericides, include sodium salts of propionic or sorbic acid, sodium diacetate, parabens, vinegar, monocalcium phosphate, or lactic acid.

Remediation and prevention of fungal growth, particularly in basements or crawl spaces are particularly important health issues in the construction industry. Depending upon the particular type of construction, and the particular geographic area in which the building is found, crawl spaces, basements, or other areas within the building may provide suitable environments for fungal and/or microbial growth. Oftentimes, basements and crawl spaces are not adequately ventilated contributing to growth of mold/microbes. In new construction, crawl spaces are often not ventilated until final steps in the construction allowing mold to grow and colonize at unacceptable levels. The mold may quickly spread to other areas within the building. This mold poses a health hazard to many individuals.

Current methods to remediate such mold problems may be expensive and structurally intrusive. In some cases, it may be necessary to remove and replace construction materials that have been sufficiently invaded with the mold or microbe.

Therefore, it can be seen that there is a need to prevent mold or microbial growth and to remediate buildings which have such mold/microbial problems.

SUMMARY OF THE INVENTION

It is one object of the present invention to provide anti-fungal materials which may be used to prevent and remediate the growth of mold. It is yet another object of the present invention to provide a matrix or carrier which may incorporate an anti-fungal agent, the matrix or carrier being inexpensive, and easy to manufacture. It is yet another object of the present invention to provide an anti-fungal material which may be easily introduced into crawl spaces or other confined areas, and which may be easily spread over a designated area. It is yet another object of the invention to provide a natural matrix or carrier for anti-fungal and/or anti-microbial chemicals, that is also hydrophobic.

The product of the present invention may be generally defined as a mold inhibitor which is integrated within a matrix. The matrix is preferably manufactured from milo seeds which have been decorticated resulting in berry and berry particulates which may then be exposed to extrusion. An anti-fungal agent or inhibitor may be directly added to the decorticated milo prior to extrusion.

*Sorghum vulgare* is a domesticated plant well known to man. It has been hybridized since early Egyptian years and is very diversified in its hybrid state. Varieties commonly referred to as milo have few if any uses other than for animal feed. *Sorghum vulgare* is widely used in the United States as a less expensive feed grain substituted for corn or wheat. Other parts of the world, particularly Africa and Asia use sorghum for flour and human food. In the United States, milo is a particular group of sorghum hybrids that are very different than the sorghum grown in other parts of the world.

It has been found that milo may be extruded into a matrix or carrier which may then be combined with an anti-fungal agent. This matrix may be introduced into confined spaces within man-made structures to prevent and to remediate the growth of mold or other fungal growths.

The particular size and density of the extruded milo matrix pieces may be adjusted to best fit the space which is to be remediated. The extruded matrix may be a light, puffy cellular mass, incorporating the anti-fungal agent, or the extrusion process can produce a more dense, nugget-like or bead-like product which incorporates the anti-fungal agent. The size and density of the product can be adjusted by choosing a particular pressure and temperature of the extrusion process. Additionally, adjusting the moisture content of the milo will also adjust the particular size and density of a product which is produced in the extrusion.

Anti-fungal agents contemplated within the present invention include, but are not limited to the 3-deoxyanthocyanidins apigeninidin, luteolinidin, and esters of arabinosyl-5-O-apigeninidin, 5-methoxy-luteolinidin, as well as calcium propionate, y-terpinene, terpinolene, terpinen-4-ol, 1,8-cineole, p-cymene and pinene.

Milo has a number of advantages for use as a matrix in providing an anti-fungal agent. As mentioned above, milo is naturally hydrophobic. Therefore, the matrix may be used within wet or damp spaces, and the milo matrix will not easily degrade milo is also flame resistant and will not pose an additional fire hazard to building structures. In its extruded state, milo is odorless, and has excellent storage characteristics which allow the milo matrix to be stored for long periods of time even prior to use and does not attract rodents or insects.

In addition to anti-fungal agents, it is also contemplated that the milo matrix of the present invention be combined with anti-microbial agents to include anti-bacterial agents or bacteriostatic agents.

In accordance with the method of the present invention, a method of making the milo matrix is disclosed. A desired stock of milo grain is chosen, and the selected grain is cleaned and sized. A de-stoning operation may be incorporated to remove any hard material, such as small stones or pebbles. The milo grain is then decorticated in one of several known methods of grain decorticating. The decortication removes the husks or hulls of the milo seeds. Optionally, the remaining berry and berry particulates may be passed through a scourer to remove the fatty endogerm portion of the berries. Defatting of the berries can enhance the ability of the milo grain to be extruded because fat can act as a lubricant in extrusion thereby degrading the ability of an extruder to produce a consistent matrix. In the extrusion, a bake-type extruder is used to apply the necessary heat and pressure. The product produced in the extrusion process can be defined as a matrix of milo which carries an anti-microbial or anti-fungal agent. One final step which may be required in the process is to cure the matrix. Curing allows the matrix to achieve equilibrium in terms of moisture content.

Alternatively, the anti-microbial/anti-fungal agents may be added to the matrix after extrusion by spraying or soaking the extruded matrix in a solution of the agent. This is less preferred and generally involves more processing and is therefore more expensive. However, embodiments of the methods of the present invention that involve post-extrusion addition of the anti-microbial/anti-fungal agents may be necessary when adding an agent that will be substantially degraded or destroyed during the extrusion process. When chemicals are used that are adversely affected by the temperatures and pressures to which the chemicals are exposed during the extrusion process, the chemicals can be added to the matrix after extrusion by soaking or spraying the extruded matrix with a solution containing the chemicals.

Other features and advantages of the present invention will become apparent from a review of the following detailed description, taken in conjunction with the drawing which illustrates a preferred embodiment of the method of the present invention.

BRIEF DESCRIPTION OF THE DRAWING

FIG. 1 is a flow chart showing the basic steps used in processing milo grain according to the present invention to produce a milo matrix which may be combined with anti-microbial or anti-fungal agents.

DETAILED DESCRIPTION

Referring to FIG. 1, basic steps in the method of making the matrix of the present invention are illustrated. In a first step at block 10, preferably, a pure stock of a milo grain is selected. Although there is no specific hybrid of milo which is required for the product and method of the present invention, it is desirable to choose a single pure stock grain because this pure stock grain is advantageous in creating consistency and repeatability of the extrusion process. Through testing, it has been found that a few particular hybrids of milo are particularly adapted for extrusion. Three hybrid varieties which have shown great success include Triumph 65G, Asgrow Seneca; and Dekalb 5400. These three hybrid varieties are well known grain stocks for use in animal feed, and are commercially available in the U.S. Although these three hybrids are preferred, it shall be understood that there may be a number of other hybrid varieties of milo which are also adapted for consistent and repeatable extrusion.

The next step in the process shown at block 12 is to clean and size the milo grain. Standard cleaning and sizing equipment may be used to process the grain at this step. For example, air/water streams may be used to clean the grain, and the grain may be passed through various sieves to obtain the desired grain size. In the present invention however, there is no particular grain size required and multiple grain sizes may be used.

Shown at block 14 is the next step in the process which is an optional destoning operation to remove stones or other similar sized objects which may still remain in the grain after cleaning and sizing. Although a destoning operation is shown as a separate optional step, destoning can be incorporated within the cleaning and sizing of the grain at step 12.

The next step in the process is shown at block 16 which is the decortication of the milo grain. Anyone of several methods of usual grain decortication may be used to decorticate the milo. Two references which disclose methods for decorticating milo and which have been found to be particularly effective are the methods described in the U.S. Pat. Nos. 5,713,526 and 5,820,039. These two references are incorporated herein by reference for purposes of disclosing basic methods by which milo grain may be decorticated.

The next step in the method is shown at block 18 which is an optional step of scouring the grain to remove fatty oils or lipids. In order to enhance the consistency and repeatability of the extrusion process, the fatty endogerm of the milo may be removed because this fatty portion of the grain tends to act as a lubricant through the extrusion die thereby degrading extruder operation. Well known grain scouring processes may be used to remove the fatty endogerm from the milo grain. Although scouring is discussed as a step in the basic method, it shall be understood that scouring is not necessarily required as it may be desirable to have certain levels of fat within the matrix. Additionally, scouring may be eliminated to simplify the overall production process.

The next step in the method is shown at block 20 which involves the introduction of a desired anti-fungal/anti-microbial agent to the processed milo. The milo combined with the anti-fungal/anti-microbial agent are referred to as a grain mix. There are a number of anti-fungal/anti-microbial agents which are contemplated within the present invention which may be used for inhibiting mold growth, or inhibiting growth of microbes.

Many naturally occurring plant products have been identified that possess significant anti-fungal and anti-bacterial activity. For example, the terpenes are isomeric hydrocarbons found primarily in essential oils, resins and balsams that possess strong anti-fungal activity. Thus, terpenes and especially y-terpinene, terpinolene, terpinen-4-ol, as well as 1,8-cineole, p-cymene and pinene are preferred anti-fungal agents for use in the construction materials of the present invention.

Additionally, phytoalexins found in sorghum are induced after the plant is exposed to fungal pathogens. The most active phytoalexins include apigeninidin, luteolinidin, a caffeic acid ester of arabinosyl-5-O-apigeninidin, and 5-methoxy-luteolinidin. Thus, these natural mold inhibitors are found within the milo grain itself. For example, in red milo, the major pigments found in the hulls of this sorghum are apigeninidin and luteolinidin. Therefore, it is also contemplated within the present invention to recover the hulls of the grain which are removed during decortication and then process the hulls to extract the apigeninidin and luteolinidin. These removed pigments can then be added back to the decorticated grain prior to extrusion and used as the anti-fungal agents.

Calcium propionate is another compound known to have significant anti-fungal activity and is compatible with the naturally occurring plant products listed above. Thus, the construction materials of the present invention include an extruded milo matrix incorporating anti-fungal compounds including calcium propionate, at least one terpene and at least one phytoalexin. Preferably, the construction material incorporates at least one of calcium propionate, apigeninidin, luteolinidin, a caffeic acid ester of arabinosyl-5-O-apigeninidin, 5-methoxy-luteolinidin, y-terpinene, terpinolene, terpinen-4-ol, 1,8-cineole, p-cymene and/or pinene in an extruded milo matrix. Depending on the intended use and storage conditions of the construction material each of these individual ingredients may be included in an amount of between about 0% to about 50% on a weight/weight basis in the extruded milo matrix. That is, each of the individual ingredients listed above may be absent or may be present in a concentration as high as 50% w/w of the extruded milo matrix. Particularly preferred embodiments of the present invention are described in Table 1 which lists the amounts of the active and inactive ingredients in the construction materials. The inactive ingredients represent the extruded milo matrix which includes amylosepectin starch, calcium, potassium, phosphorus, sulfur, manganese and ash. The water content of the material, if any, is not shown in Table 1.

TABLE 1

| Ingredient | Amount |
|---|---|
| Inactive Ingredients (Extruded Milo Matrix) | |
| starch, Ca, K, Ph, S, Mn, ash | 86%–94% |
| Active Ingredients | |
| Calcium propionate | 4%–8% |
| y-terpinene | 0.1%–0.8% |
| terpinolene | 0.03%–0.3% |
| 1,8-cineole | 0.01%–0.6% |
| p-cymene | 0.05%–0.7% |
| α-pinene | 0.02%–0.4% |
| apigeninidin | up to 0.01% |
| luteolinidin | up to 0.01% |

In order to provide an extrudable mixture, it is preferable to maintain the milo at or around 16% moisture content prior to extrusion. Accordingly, an amount of water must be added to the decorticated milo prior to extrusion. Depending upon the type of agent which is added to the decorticated milo, a lesser or greater amount of water must be added to bring the moisture content of the milo grain mix to preferably around 16% moisture.

It may be desirable to mechanically mix the grain mix in a bin which will then meter the grain mix into the extrusion machine. Mechanical mixing helps to ensure uniform dispersion of the added agent.

The next step in the method is illustrated at block 22 which involves extrusion of the milo grain mix. Through testing, it has been found that extrusion can be achieved utilizing a bake-type extruder which exposes the grain mix to heat in the range of about 325° F. to about 400° F. and pressure in the range of between about 1500 and about 2000 psi. The particular shape of the die used in the extruding machine may be adapted to produce a matrix of a desired shape. One example is a die having a round shaped hole with a diameter of approximately 0.120 of an inch. The cutting mechanism used in the extruding machine could be adapted for cutting the extrudate to a length of approximately three-quarters of an inch. The resulting extruded product can be of different sizes and densities. For example, if a particularly small enclosed space must be remediated by introduction of the matrix, it may be desirable to provide the matrix in a more dense extrudate. Accordingly, the extrudate could have a smaller size and a nugget-like consistency. If the area to be remediated had not yet developed fungal or microbial problems and the purpose of introducing the matrix was primarily for prevention, then it may be adequate to provide the matrix in a larger sized, lighter, puffier extrudate. The amount of the anti-fungal/anti-microbial agent in the denser, nugget-like extrudate would be greater since more matrix is used per piece of extrudate while the amount of the anti-fungal/antimicrobial agent would be more dispersed within the lighter, puffy extrudate. Since the concentration of the anti-fungal/antimicrobial agent can vary depending upon the density of the extrudate, the extrudate can be tailored for each application. Of course, one could also simply vary the amount of the agent used when it is initially mixed with the decorticated milo to provide the desired concentration of the agent in the matrix.

The last step of the method is shown at block 24 which contemplates curing the matrix product to thereby stabilize the product prior to storage and shipping. Depending upon the matrix produced, i.e., one which is either puffed or more dense, a certain amount of curing may be required to allow the matrix to reach equilibrium in terms of moisture content.

There are a number of advantages of utilizing a milo matrix as a carrier for an anti-fungal and/or anti-microbial agent. First, the extruded milo is naturally hydrophobic which therefore allows the milo matrix to be used in damp or wet spaces for extended periods of time without substantial decay. Milo is a readily available grain source, and is relatively inexpensive compared to man made or artificial compositions. Another advantage as mentioned above is the ability to produce a matrix which has a variety of sizes and densities by simply altering the moisture content of the grain mix prior to extrusion. By altering the density, the concentration of the agent may also be adjusted. After extrusion, the milo matrix contains some percentage of carbohydrates; however, the matrix is very low in nutritional value, and has little odor. The matrix has no detectable amounts of sugars, less than 2% fat and less than 10% protein. Therefore, the matrix does not attract rodents or insects.

The matrix of the present invention is easily deployed within many commercial structures by simply transporting the matrix to a desired location, and spreading the matrix within the desired space to be remediated or for prevention of mold and/or microbial growth. For prevention of mold, it has been found that spreading a layer of 3–6 inches of the lighter, puffier, matrix over the targeted area is adequate for preventing mold growth. For remediation of mold, it may be necessary to increase the depth of the spread matrix, and it may also be necessary to increase the density of the matrix at a particular location. As best understood, there are two primary ways in which the agent inhibits mold or microbial growth. The first is physical contact of the matrix with the area to be remediated. The second is production of an off-gas through sublimation of the additive into the atmosphere enclosed by the space to be remediated. For example, with chlorine, a certain amount of the solid chlorine will off-gas producing a vapor which prevents mold growth. Of course, the concentration of the chlorine in the milo matrix has to be controlled so that the off gas produced does not reach dangerous levels.

It may be necessary over time to add additional amounts of the matrix to the area to be remediated. As the agent continues to sublime or otherwise chemically break down, the concentration of the agent will diminish.

The present invention has been described with respect to a preferred embodiment however, other changes and modifications may be made to the invention within the spirit and scope thereof.

What is claimed is:

1. A composition comprising a decorticated milo grain seed and chemicals selected from the group consisting of calcium propionate, y-terpinene, terpinolene, terpinen-4-ol, 1,8-cineole, p-cymene, α-pinene, apigeninidin, luteolinidin and combinations thereof, with the proviso that when said composition comprises calcium propionate, the amount of said calcium propionate in said composition is between about 4% and about 8% by weight.

2. The composition of claim 1 comprising between about 0.1% and about 0.8% y-terpinene by weight.

3. The composition of claim 1 comprising between about 0.03% and about 0.3% terpinolene by weight.

4. The composition of claim 1 comprising between about 0.01% and about 0.6% 1,8-cineole by weight.

5. The composition of claim 1 comprising between about 0.05% and about 0.7% p-cymene by weight.

6. The composition of claim 1 comprising between about 0.02% and about 0.4% α-pinene by weight.

7. The composition of claim 1 comprising less than about 0.01% apigeninidin by weight.

8. The composition of claim 1 comprising between about 0.01% luteolinidin by weight.

9. A method of making the composition of claim 1 comprising:
 decorticating a milo grain;
 mixing the decorticated grain with a chemical selected from the group consisting of calcium propionate, y-terpinene, terpinolene, terpinen-4-ol, 1,8-cineole, p-cymene, α-pinene, apigeninidin, luteolinidin and combinations thereof to form a grain mix; and,
 extruding the grain mix.

10. The method of claim 9, wherein the moisture content of the grain mix prior to extrusion is adjusted to about 16%.

11. The method of claim 9, wherein the milo grain is scoured prior to extrusion.

12. The method of claim 9, wherein the milo grain is de-stoned prior to extrusion.

13. The method of claim 9, wherein the grain mix is cured after extrusion.

14. A method of making the composition of claim 1 comprising:
 decorticating a milo grain;
 extruding the decorticated milo grain; and,
 contacting the extruded milo grain with a chemical selected from the group consisting of calcium propionate, y-terpinene, terpinolene, terpinen-4-ol, 1,8-cineole, p-cymene, α-pinene, apigeninidin, luteolinidin and combinations thereof.

15. The method of claim 14, wherein the contacting step comprises soaking the extruded milo grain in a solution containing the chemical.

16. The method of claim 14, wherein the contacting step comprises spraying the extruded milo grain in a solution containing the chemical.

17. A composition comprising a decorticated milo grain seed and chemicals selected from the group consisting of y-terpinene, terpinolene, terpinen-4-ol, 1,8-cineole, p-cymene, α-pinene, apigeninidin, luteolinidin and combinations thereof.

18. The composition, of claim 17, wherein the group further consists of calcium propionate between about 4% and about 8% by weight.

19. The composition of claim 17 comprising between about 0.1% and about 0.8% y-terpinene by weight.

20. The composition of claim 17 comprising between about 0.03% and about 0.3% terpinolene by weight.

21. The composition of claim 17 comprising between about 0.01% and about 0.6% 1,8-cineole by weight.

22. The composition of claim 17 comprising between about 0.05% and about 0.7% p-cymene by weight.

23. The composition of claim 17 comprising between about 0.02% and about 0.4% α-pinene by weight.

24. The composition of claim 17 comprising less than about 0.01% apigeninidin by weight.

25. The composition of claim 17 comprising between about 0.01% luteolinidin by weight.

26. A method of making the composition of claim 17 comprising:
 decorticating a milo grain;
 mixing the decorticated grain with a chemical selected from the group consisting of y-terpinene, terpinolene, terpinen-4-ol, 1,8-cineole, p-cymene, α-pinene, apigeninidin, luteolinidin and combinations thereof to form a grain mix; and,
 extruding the grain mix.

27. The method of claim 26, wherein the moisture content of the grain mix prior to extrusion is adjusted to about 16%.

28. The method of claim 26, wherein the milo grain is scoured prior to extrusion.

29. The method of claim 26, wherein the milo grain is de-stoned prior to extrusion.

30. The method of claim 26, wherein the grain mix is cured after extrusion.

31. A method of making the composition of claim 17, comprising:
 decorticating a milo grain;
 extruding the decorticated milo grain; and,
 contacting the extruded milo grain with a chemical selected from the group consisting of y-terpinene, terpinolene, terpinen-4-ol, 1,8-cineole, p-cymene, α-pinene, apigeninidin, luteolinidin and combinations thereof.

32. The method of claim 31, wherein the contacting step comprises soaking the extruded milo grain in a solution containing the chemical.

33. The method of claim 31, wherein the contacting step comprises spraying the extruded milo grain in a solution containing the chemical.

* * * * *